United States Patent [19]

Yamamoto et al.

[11] Patent Number: 5,112,987

[45] Date of Patent: May 12, 1992

[54] PROCESS FOR THE PREPARATION OF INDIGO COMPOUNDS

[75] Inventors: Yoshihiro Yamamoto, Yokohama; Usaji Takaki, Fujisawa; Shinobu Aoki; Isao Hara, both of Yokohama, all of Japan

[73] Assignee: Mitsui Toatsu Chemicals, Inc., Tokyo, Japan

[21] Appl. No.: 426,375

[22] Filed: Oct. 25, 1989

Related U.S. Application Data

[63] Continuation-in-part of Ser. No. 314,021, Feb. 23, 1989, Pat. No. 4,992,556, and a continuation-in-part of Ser. No. 324,503, Mar. 16, 1989, Pat. No. 4,966,977, and a continuation-in-part of Ser. No. 343,459, Apr. 25, 1989, Pat. No. 4,973,706.

[30] Foreign Application Priority Data

Apr. 25, 1988 [JP] Japan .................. 63-100214
Nov. 10, 1988 [JP] Japan .................. 63-282515
Nov. 11, 1988 [JP] Japan .................. 63-283750

[51] Int. Cl.⁵ .................................................. C07D 403/04
[52] U.S. Cl. ............................................ 548/457; 548/455; 548/454
[58] Field of Search ............................................ 548/457

[56] References Cited

PUBLICATIONS

Witkof et al., Jr. Am. Chem. Soc., 73, 713 (1951).
Witkof, Ann., 558, 98 (1947).

*Primary Examiner*—David B. Springer
*Attorney, Agent, or Firm*—Millen, White & Zelano

[57] ABSTRACT

A process for the preparation of an indigo compound which comprises reacting a corresponding indole compound having no substituent at the 2- and 3-positions with a percarboxylic acid in the presence of an alcohol solvent, or with heating over 60° C. in the presence of an aprotic solvent.

28 Claims, No Drawings

1

PROCESS FOR THE PREPARATION OF INDIGO COMPOUNDS

This is a continuation-in-part of application Ser. No. 07/314,021, filed Feb. 23, 1989, now U.S. Pat. No. 4,992,556; of application Ser. No. 07/324,503, filed Mar. 16, 1989, now U.S. Pat. No. 4,966,977; and of application Ser. No. 07/343,459, filed Apr. 25, 1989, now U.S. Pat. No. 4,973,706.

BACKGROUND OF THE INVENTION

1. Field of the Invention

This invention relates to a process for the preparation of an indigo compound. More specifically, it relates to a process for the preparation of an indigo compound by reacting an indole compound having no substituent at the 2- and 3-positions with a percarboxylic acid in the presence of a specific solvent.

2. Description of the Related Art

Indigo compounds are important compounds that are useful as dyes. The presently employed industrial processes for the preparation of indigo comprise forming an N-phenylglycine salt from aniline and chloroacetic acid, or from aniline, cyanic acid and formaldehyde, converting this salt into an indoxyl compound by alkali fusion at elevated temperature, and then oxidizing this compound with air. However, these processes are not only complicated ones involving many steps, but also require the use of large amounts of potassium hydroxide and sodium hydroxide. Moreover, the recovery and reuse of used potassium hydroxide and sodium hydroxide has the disadvantage of consuming much energy and requiring special equipment. Therefore, conversion to a simpler process has been desired.

Meanwhile, there is a report that indole have been reacted with perbenzoic acid, which is a percarboxylic acid, in chloroform as a solvent by allowing the reaction mixture to stand in a refrigerator overnight (Justus Liebigs Annalen der Chimie, Vol. 558, pp. 91-98, 1947). According to the article, it has been reported that o-formaminobenzaldehyde was produced together with a variety of other products, and a very small amount of indigo was also formed at the same time. Moreover, there is another report that peracetic acid, which is a percarboxylic acid, was produced from hydrogen peroxide and acetic acid in the reaction system and reacted with indole in acetic acid as a solvent (Bull. Agr. Chem. Soc. Japan, Vol. 20, pp. 80-83, 1956). According to the report, it has been reported that 2,2-diindyl-$\psi$-indoxyl, which is a trimer of indole skeleton, was produced as a main product and in addition a very small amount of indigo was formed as a by-product. However, each of these reports was concerned with a brief investigation on the reactivity of indole, main products were o-formaminobenzaldehyde and 2,2-diindyl-$\psi$-indoxyl, respectively, and indigo, which is the desired product in the present invention, was nothing but a by-product formed in very low yield.

In application Ser. No. 07/314,021, filed Feb. 23, 1989, filed by us and another, the conversion of an indigo compound lacking 2- and 3-position substituents to an indigo compound is achieved with an organic hydroperoxide; in our Ser. No. 07/324,503, it is achieved with hydrogen peroxide; in our Ser. No. 07/343,459, it is achieved with an organic hydroperoxide in the presence of a carboxyl compound or a boric acid ester compound as an additive.

SUMMARY OF THE INVENTION

It is an object of the present invention to provide an improved and simple process for the preparation of indigo compounds.

It is another object of the present invention to provide a process for the preparation of indigo compounds which uses an indole compound as a starting material and can achieve higher efficiency than the above-described prior art processes.

The present inventors have carried on an exhaustive investigation on methods for producing an indigo compound efficiently by reacting an indole compound with a percarboxylic acid. As a result, it has now been found that the field of an indigo compound is increased sharply, if a specific liquid medium is employed when reacting an indole compound with a percarboxylic acid. The present invention has been completed on the basis of these findings.

According to the present invention, there is provided a process for the preparation of an indigo compound which comprises reacting a corresponding indole compound having no substituent at the 2- and 3-positions with a percarboxylic acid in the presence of an alcohol solvent, or reacting them with heating over 60° C. in the presence of an aprotic solvent.

DESCRIPTION OF THE PREFERRED EMBODIMENTS

The indole compound having no substituent at the 2- and 3-positions, which is used as one of the starting materials in the process of the present invention, is selected from the group consisting of indole; alkylindoles having 1 to 4 alkyl groups of 1 to 10 carbon atoms, such as 1-methylindole, 4-ethylindole, 5-methylindole, 6-methylindole, 6-isopropylindole, 7-methylindole and 4,5-dimethylindole; cycloalkylindoles having 1 to 4 cycloalkyl groups of 3 to 12 carbon atoms, such as 4-cyclohexylindole and 5-cyclopentylindole; arylindoles having 1 to 4 unsubstituted or alkyl-substituted aryl groups of 6 to 30 carbon atoms, such as 5-phenylindole and 6-$\beta$-naphthylindole; halogenated indoles having 1 to 4 halogen atoms, such as 4-chloroindole, 5-chloroindole, 5,7-dichloroindole, 5-bromoindole, 6-bromoindole, 5,7-dibromoindole and 4-chloro-5-bromoindole; hydroxyindoles having 1 to 4 hydroxyl groups, such as 4-hydroxyindole, 5-hydroxyindole and 4,5-dihydroxyindole; alkoxyindoles having 1 to 4 alkoxy groups of 1 to 10 carbon atoms, such as 4-methoxyindole and 5-benzyloxyindole; phenoxyindoles having 1 to 4 phenoxy groups of 6 to 30 carbon atoms, such as 5-phenoxyindole; halogenated alkylindoles having 1 to 3 halogen atoms and 1 to 3 alkyl groups of 1 to 10 carbon atoms, such as 4-chloro-5-ethylindole, 6-chloro-4-methylindole, 4-bromo-5-ethylindole and 5-bromo-4-methylindole; nitroindoles having 1 to 4 nitro groups, such as 4-nitroindole, 5-nitroindole and 7-nitroindole; acylindoles having 1 to 4 acyl groups of 2 to 20 carbon atoms, such as 1-benzoylindole and 4-acetylindole; acyloxyindoles having 1 to 4 acyloxy groups of 2 to 20 carbon atoms, such as 1-acetoxyindole and 4-benzoyloxyindole; indolecarboxylic acids, such as indole-5-carboxylic acid, and esters thereof; N,N-dialkylaminoindoles having 1 to 4 N,N-dialkylamino groups in which each alkyl group contains 1 to 10 carbon atoms, such as 5-N,N-dimethylaminoindole; and sulfonated indoles. Of course, these indole compounds should not have the above-described substituent groups at the 2- and 3-positions. In addition, indole compounds having a combination of two or more types of substituent groups as described above are also useful in the process of the present invention. At positions other than the 2- and 3-positions, these indole compounds may have any substituent that does not interfere with the reaction. Among these indole compounds, indole is especially preferred.

The percarboxylic acid, which is used as the other starting material in the process of the present invention, is an organic compound having at least one percarboxyl (—COOOH) group. Useful percarboxylic acids are listed, for example, in the tables given in D. Swern, "Organic Peroxides, Vol. I", Wiley-Interscience (1970), pp. 401–403 and pp. 436–445. Among these percarboxylic acids, peraliphatic acids such as peracetic acid and perpropionic acid, and perbenzoic acid derivatives such as perbenzoic acid, m-chloroperbenzoic acid, p-chloroperbenzoic acid, o-methyl perbenzoic acid and p-isopropyl perbenzoic acid, are preferred.

These percarboxylic acids may be used alone, or two or more of them may be used in admixture or in sequence. Alternatively, it is also possible to use a suitable combination of components (e.g., hydrogen peroxide and a carboxylic acid) which can produce such a percarboxylic acid in the reaction system. Although the amount of percarboxylic acid used is not critical, it is usually in the range of about 0.01 to about 100 moles, preferably about 0.1 to about 20 moles, per mole of the indole compound.

The alcohol solvents according to the process of the present invention are listed, for example, in Shozo Asahara et al. (ed.), "Solvent Handbook", the first edition, Kodansha (1976), pp. 327–420. Preferred alcohol solvents are, for example, methanol, ethanol, 1-propanol, 1-butanol, tert-butanol, 1-hexanol, 2-octanol, allyl alcohol, benzyl alcohol, cyclohexanol, 1,2-ethanediol, 1,4-butanediol, glycerol and the like. These solvents may be used alone or in admixture of two or more.

The aprotic solvents according to the process of the present invention are defined compounds as a solvent which is incapable of donating proton itself and does not self-dissociate, in Shozo Asahara et al. (ed.), "Solvent Handbook", the first edition, Kodansha (1976), pp. 25. The aprotic solvents usable in the present invention are not limited by the examples described above, and examples thereof include aliphatic and alicyclic hydrocarbons such as n-hexane, 2-methylpentane, n-octane, isooctane, cyclohexane, bicyclohexyl and p-menthane; aromatic hydrocarbons such as benzene, toluene, xylene, ethylbenzene, cumene, p-cymene and naphthalene; aliphatic and aromatic halogen compounds such as chloroform, carbon tetrachloride, 1,2-dichloroethane, chlorobenzene, bromobenzene, chlorotoluene and dichlorobenzene; ethers such as dipropyl ether, diphenyl ether, tetrahydrofuran, ethylene glycol diethyl ether and phenetole; ketones such as methyl ethyl ketone, 2-hexanone, acetonylacetone and acetophenone; esters such as propyl acetate, ethyl propionate, methyl benzoate and dimethyl phthalate; carbonates such as diethyl carbonate and propylene carbonate; aliphatic and aromatic nitro compounds such as nitroethane and nitrobenzene; and nitriles such as acetonitrile and benzonitrile. These solvents may be used alone or in admixture of two or more.

In the process of the present invention, no particular limitation is placed on the method by which the reaction is carried out. There may be employed in any of batch, semibatch and continuous operations. More specifically, there may be employed a method in which the indole compound and percarboxylic acid together with liquid medium are charged into a reactor all at once, a method in which materials are continuously fed to a reactor all at once, a method in which a mixture of liquid medium and one material is continuously or intermittently fed with the other material, and a method in which liquid medium is continuously or intermittently, at the same time or alternately, fed with each of these materials.

In the case where alcohol solvent is used as liquid medium, the reaction temperature is usually in the range of about −10° C. to about 170° C. If the reaction temperature is lower than the lowest limit, the reaction will become unduly slow, while if it is higher than the supremum, the reaction may be attended with danger because of violent decomposition of the percarboxylic acid. Preferably, the reaction temperature is in the range of about 10° C. to about 150° C., particularly about 60° C. to about 150° C.

In the case where aprotic solvent is used as liquid medium, the reaction temperature is important. The reaction is carried out over 60° C. with heating. If the reaction temperature is lower than this temperature, the reaction will not only be slow, but the formation of indigo is also depressed extremely. Preferably, the reaction temperature is continually kept over 60° C. from the beginning to the end. Particularly, it is in the range of about 60° C. to about 150° C.

The reaction time is usually within about 50 hours and preferably in the range of about 0.01 to about 20 hours. According to circumstances, the reaction may be carried out under reduced, atmospheric or superatmospheric pressure.

In the process of the present invention, the reaction may be carried out in an atmosphere of inert gas or in the presence of molecular oxygen such as air.

In the process of the present invention, a metallic compound catalyst capable of oxidizing the carbon atom at the 3-position of the indole compound and/or a promotor can be used for enhancing the yield and selectivity of the indigo compound and the reaction rate. The term "metallic compound catalyst capable of oxidizing the carbon atom at the 3-position of the indole compound" comprehends compounds of metals which, in the reaction of the indole compound with the percarboxylic acid, can cause the carbon atom at the 3-position of the indole compound to be oxidized by an oxygen atom.

For example, this catalyst is at 1 one compound selected from the group consisting of compounds of the metals of groups 4A, 5A and 6A of the table, manganese, silver and aluminium, in which they are used for a reaction of epoxidizing olefins; the metals of the iron group, the platinum group, copper and zinc, in which they are used for a ketogenic reaction of olefins or alcohols. Specifically, compounds of the metals of group 4A, 5A and 6A of the periodic table various compounds of titanium, zirconium, hafnium, vanadium, niobium, tantalum, chrominum, molybdenum and tungsten. Similarly, the compound of the iron group includes compounds of iron, cobalt and nickel, and the compounds of the platinum group includes compounds of ruthenium, rhodium, palladium, osmium, iridium and platinum. More specifically, they include inorganic compounds of the aforesaid metals, such as halides, oxyhalides, oxides, mixed oxides, sulfides, borides, phosphides, hydroxides, oxyhydroxides, cyano complexes, inorganic acid salts (e.g., sulfates, nitrates and phosphates), metallic oxyacids (e.g., titanic acid, molybdic acid and tungstic acid) and salts thereof, and heteropoly-acids (e.g., phosphomolybdic acid and silicotungstic acid) and salts thereof; compounds of the aforesaid metals having an organic group in at least a portion thereof, such as organic acid salts (e.g., acetates, oxalates, benzoates and naphthenates), alkoxides (e.g., those derived from ethyl alcohol and isopropyl alcohol), phenoxides (e.g., those derived from phenol and m-chlorophenol), and halogen compounds having an alkoxy or phenoxy group; complex compounds of the aforesaid metals, such as carbonyl complexes, amine complexes, pyridine complexes (e.g., those derived from pyridine and bipyridyl) oxo complexes, thiolate complexes (e.g., those derived from cysteine and dithiocatechol), sulfide complexes, dithiocarbamate complexes, thiocyanate complexes, isocyanate complexes, nitrosyl complexes, phosphine complexes (e.g., those derived from triphenylphosphine and 1,2-diphenylphosphinoethane), phosphoryl complexes, phthalocyanine complexes, porphyrin complexes, nitrile complexes, ether complexes, ketone complexes, β-ketocarbonyl complexes (e.g., those derived from acetylacetone), alkyl and allene complexes, olefin complexes and cyclopentadienyl complexes; and compounds of the aforesaid metals coming under two or more of the foregoing categories.

Moreover, they include catalysts which carry the aforesaid metals on carriers such as active carbon, silica gel, alumina, silica-alumina, diatomaceous earth, magnesia, pumice and molecular sieve, or Raney catalysts.

These metallic compounds may be used alone or in admixture of two or more. It is also possible to use a suitable combination of components which produce any of these metallic compounds in the reaction system. Although these metallic compounds are preferably soluble in the reaction mixture, they may be partially or totally insoluble therein. These metallic compounds are usually used in an amount of not greater than 0.5 mole, preferably 0.00001 to 0.1 mole, per mole of the indole compound.

The promotor used in the process of the present invention includes, for example, dehydrating agents such as silica gel, sodium sulfate, methyl orthoformate, acetic anhydride and molecular sieve; radical scavengers such as phenol, tert-butylcatechol, 2,6-di-tertbutylphenol, 3 tert-butyl-4-hydroxy-5-methyl phenyl sulfide, benzoquinone and hydroquinone; ligands of catalytic metals such as phosphines and phosphates (e.g., triphenylphosphine, 1,2-diphenylphosphinoethane, triisopropoxyphosphine and triphenyl phosphate), arsenic compounds (e.g., arsenic triphenyl), amines (e.g.,dimethyl amine and triethyl amine), and pyridines (e.g., pyridine, quinoline, acridine, dipyridyl and phenanthroline); boric acid esters and metaboric acid esters such triethyl borate, triisopropyl borate, tricumyl borate, cyclohexyl metaborate, phenyl metaborate and menthyl metaborate; salts of alkaline metals and alkaline earth metals with organic or inorganic acids, such as lithium acetate, lithium iodide, sodium acetate, sodium carbonate, potassium nitrate, potassium benzoate, barium sulfate, barium chloride, barium propionate, and magnesium acetate; salts of rare earth metals such as cerium acetate and lanthanum acetate; stabilizers for oxidixzing agents, such as sodium carbonate, sodium stannate, barbital, 8-hydroxyquinoline, uric acid, hippuric acid, acetanilide, phenacetin, phosphoric acid, ethylenediaminetetraacetic acid disodium salt and sodium picrate; producers of adducts with oxidizing agents, such as nitriles (e.g., acetonitrile, adiponitrile and benzonitrile), isocyanates (e.g., phenylisocyanate), ureas (e.g., tetramethylurea and 1,1'-carbonyl bis(1,2,4-triazole)) and diisopropylcarbodiimide; trimethyl dichloroantimony, tetramethyltin, di-n-butyl dichlorotin, pyrimidine and cyanuric acid. Among those, dehydrating agents, radical scavengers, ligands of catalytic metals, boric acid esters and metaboric acid esters, salts of alkaline metals and alkaline earth metals with organic or inorganic acids, and salts of rare earth metals are preferred. These promoters may be used alone, or in admixture of two or more. These promotors are usually used in an amount of not greater than 50 moles, preferably in the range of 0.001 to 20 moles, per mole of the indole compound.

In the process of the present invention, the desired indigo compound can be obtained by working up the resulting reaction mixture in the usual manner. On completion of the reaction, most of the formed indigo compound has usually precipitated out. Therefore, the indigo compound can easily be recovered as a solid according to a conventional solid-liquid separation technique such as filtration, centrifugation or decantation. Where the amount of the precipitated indigo compound is insufficient, it is also possible to concentrate the reaction mixture and then recover the resulting increased amount of precipitate therefrom.

The present invention is further illustrated by the following examples. These examples are intended to illustrate the invention and are not to be construed to limit the scope of the invention.

EXAMPLE 1

A four neck flask having a capacity of 100 ml and fitted with a stirrer, a thermometer, a dropping funnel and a cooling coil was charged with 1.0 g (8.5 mmoles) of indole, and 17 ml (14 g) of methanol. While this mixture was being heated at 66° C. under reflux of the methanol on an oil bath and stirred, a solution of 2.95 g (17.1 mmoles) of m-chloroperbenzoic acid as a percarboxylic acid dissolved in 58 ml (46 g) of methanol was added dropwise thereto over a period of 1.5 hours. Thereafter, the reaction was continued for 3.5 hours under the same conditions. The reaction mixture was homogeneous at the start of the reaction, but a deep blue solid gradually precipitated out with the progress of the reaction. After completion of the reaction, this reaction mixture was filtered. The solid so separated was washed enough with methanol and then dried at 50° C. under reduced pressure to obtain 188 mg of a deep blue solid product. Elemental analysis and IR spectroscopic analysis revealed that this product was indigo. The molar yield of the isolated indigo as based on the charged indole (hereinafter referred to briefly as the indigo yield) was 16.8%.

COMPARATIVE EXAMPLE 1

Reaction and after-treatment were carried out in the same manner as in Example 1, except that 17 ml (18 g) and 58 ml (61 g) of acetic acid for dissolving indole and m-chloroperbenzoic acid, respectively, were used in place of the methanol, and the reaction temperature was kept at 66° C. Thus, there was obtained 35 mg of indigo. The indigo yield was 3.1%.

EXAMPLE 2

Reaction and after-treatment were carried out in the same manner as in Example 1, except that 17 ml and 58 ml of tert-butanol for dissolving indole and m-chloroperbenzoic acid, respectively, were used in place of the methanol, and the reaction temperature was changed to 80° C.

Thus, there was obtained 296 mg of indigo. The indigo yield was 26.4%.

EXAMPLE 3

1.0 g (8.5 mmoles) of indole and 35 ml of methanol were charged in a four neck flask as used in Example 1. While this mixture was being heated under reflux of the methanol on an oil bath and stirred, 1.95 g (10.3 mmoles as peracetic acid) of a 40 wt. % acetic acid solution of peracetic acid was added dropwise thereto over a period of 15 minutes. Thereafter, the reaction was continued for 5 hours under the same conditions. The resulting reaction mixture was worked up in the same manner as in Example 1. Thus, there was obtained 116 mg of indigo, and the indigo yield was 10.4%.

EXAMPLE 4

Reaction and after-treatment were carried out in the same manner as in Example 3, except that 35 ml of ethanol was used in place of the methanol, and the reaction temperature was changed to 80° C. As a result, the indigo yield was 18.3%.

COMPARATIVE EXAMPLE 2

Reaction and after-treatment were carried out in the same manner as in Example 3, except that 35 ml of acetic acid was used in place of the methanol, and the reaction temperature was changed to 80° C. As a result, the indigo yield was 3.0%.

EXAMPLE 5

A four neck flask having a capacity of 100 ml and fitted with a stirrer, a thermometer, a dropping funnel and a cooling coil was charged with 1.0 g (8.5 mmoles) of indole, and 17 ml (15 g) of toluene.

While this mixture was being heated at 80° C. on an oil bath and stirred, a solution of 2.95 g (17.1 mmoles) of m-chloroperbenzoic acid as a percarboxylic acid dissolved in 58 ml (50 g) of toluene was added dropwise thereto over a period of 1.5 hours. Thereafter, the reaction was continued for 3.5 hours under the same conditions. The resulting reaction mixture was worked up in the same manner as in Example 1. Thus, there was obtained 604 mg of indigo and the indigo was yield 54.0%.

COMPARATIVE EXAMPLE 3

Reaction was carried out in the same manner as in Example 5, except that the reaction temperature was changed to 5° C. by cooling on an ice bath. While the toluene solution of m-chloroperbenzoic acid was added dropwise, white solid precipitated out. In the time of completion of adding, the reaction mixture was suspended. Thereafter, the reaction was continued for 3.5 hours under the same conditions, but no indigo was formed. Moreover, the reaction was continued for 20 hours. After completion of the reaction, the reaction mixture was filtered. The solid so separated was washed enough with methanol to be completely dissolved. Indigo was not obtained at all.

EXAMPLE 6

Reaction and after-treatment were carried out in the same manner as in Example 5, except that the amounts of m-chloroperbenzoic acid and toluene for dissolving the m-chloroperbenzoic acid were changed to 1.77 g (10.3 mmoles) and 40 ml (35 g), respectively, and the dropping time and reaction time were changed to 1.0 hour and 4.0 hours, respectively. Then, there was obtained 404 mg of indigo. According to gas chlomatography, 462 mg (3.9 mmoles) of unreacted indole remained in the reaction solution. The indole conversion was 53.8%, the indigo yield was 36.1%. The molar yield of the isolated indigo as based on the converted indole (hereinafter referred to briefly as the indigo selectivity) was 67.1%.

EXAMPLE 7

A four neck flask as used in Example 5 was charged with 1.0 g (8.5 mmoles) of indole and 35 ml (30 g) of toluene. While this mixture was being heated at 80° C. on an oil bath and stirred, 1.95 g (10.3 mmoles as peracetic acid) of a 40 wt. % acetic acid solution of peracetic acid was added dropwise thereto over a period of 15 minutes. Thereafter, the reaction was continued for 5 hours under the same conditions. The resulting reaction mixture was worked up in the same manner as in Example 5. There was obtained 363 mg of indigo. According to the same analysis as in Example 6, the indole conversion was 79.9%, the indigo yield was 32.4% and the indigo selectivity was 40.6%.

COMPARATIVE EXAMPLE 4

Reaction, after-treatment and analysis were carried out in the same manner as in Example 7, except that the reaction temperature was changed to 5° C. by cooling on an ice bath. As a result, the indole conversion was 58.3%, the indigo yield was 0.1% and the indigo selectivity was 0.2%.

COMPARATIVE EXAMPLE 5

Reaction, after-treatment and analysis were carried out in the same manner as in Example 7, except that 35 ml of acetic acid was used in place of the toluene. As a result, the indole conversion 100%, the indigo yield was 3.0% and the indigo selectivity was 3.0%.

EXAMPLE 8

Reaction and after-treatment were carried out in the same manner as in Example 7, except that 35 ml of o-dichlorobenzene was used in place of the toluene and the reaction temperature was changed to 65° C. As a result, the indigo yield was 27.9%.

EXAMPLE 9

Reaction and after-treatment were carried out in the same manner as in Example 7, except that the amount of the 40 wt. % acetic acid solution of peracetic acid was changed to 8.12 g (42.7 mmoles as peracetic acid) and 35 ml of diphenyl ether was used in place of the toluene. As a result, the indigo yield was 23.4%.

EXAMPLE 10

Reaction and after-treatment were carried out in the same manner as in Example 7, except that 50 ml of 1,2-dichloroethane was used in place of the toluene. As a result, the indigo yield was 30.7%.

EXAMPLE 11

A four neck flask having a capacity of 200 ml and fitted with a stirrer, a thermometer, a dropping funnel and a cooling coil was charged with 1.0 g (8.5 mmoles) of indole, 29.9 mg (0.085 mmole) of tungsten hexacarbonyl, and 50 g of o-xylene. While this mixture was being heated at 80° C. on an oil bath and stirred, a solution of 2.21 g (12.8 mmoles) of m-chloroperbenzoic acid dissolved in 50 g of o-xylene was added dropwise thereto over a period of 1.5 hours. Thereafter, the reaction was continued for 3 hours under the same conditions. The resulting reaction mixture was worked up in the same manner as in Example 1.

Thus, there was obtained 0.49 g of indigo. The indigo yield was 43.8%.

EXAMPLE 12

Reaction and after-treatment were carried out in the same manner as in Example 11, except that 30.6 mg (0.085 mmole) of 3 tert-butyl-4-hydroxy-5-methyl phenyl sulfide was used in place of the tungsten hexacarbonyl. Thus, there was obtained 0.51 g of indigo. The indigo yield was 45.6%.

EXAMPLE 13

Reaction was carried out in the same manner as in Example 11, except that 45.2 mg (0.43 mmole) of sodium carbonate was used in place of the tungsten hexacarbonyl. After completion of the reaction, the resulting reaction mixture was filtered. The solid so separated was washed enough with water and methanol and then dried at 50° C. under reduced pressure to obtain 0.47 g of indigo. The indigo yield was 42.0%.

What is claimed is:

1. A process for the preparation of an indigo compound which comprises reacting a corresponding indole compound having no substituent at 2- and 3-positions with a percarboxylic acid in a solvent consisting essentially of an alcohol solvent or with heating to over 60° C. in an aprotic solvent.

2. A process as claimed in claim 1 wherein the reaction is conducted in an alcohol solvent.

3. A process as claimed in claim 2, wherein the indole compound having no substituent at 2- and 3-positions is a compound selected from the group consisting of indole, alkylindoles having 1 to 4 alkyl groups of 1 to 10 carbon atoms, cycloalkylindoles having 1 to 4 cycloalkyl groups of 3 to 12 carbon atoms, arylindoles having 1 to 4 unsubstituted or alkyl-substituted aryl groups of 6 to 30 carbon atoms, halogenated indoles having 1 to 4 halogen atoms, hydroxyindoles having 1 to 4 hydroxyl groups, alkoxy indoles having 1 to 4 alkoxy groups of 1 to 10 carbon atoms, phenoxyindoles having 1 to 4 phenoxy groups of 6 to 30 carbon atoms; halogenated alkylindoles having 1 to 3 halogen atoms and 1 to 3 alkyl groups of 1 to 10 carbon atoms, nitroindoles having 1 to 4 nitro groups, acylindoles having 1 to 4 acyl groups of 2 to 20 carbon atoms, acyloxyindoles having 1 to 4 acyloxy groups of 2 to 20 carbon atoms; indolecarboxylic acids and esters thereof, N,N-dialkylaminoindoles having 1 to 4 N,N-dialkylamino groups in which each alkyl group contains 1 to 10 carbon atoms, and sulfonated indoles.

4. A process as claimed in claim 2 wherein the indole compound having no substituent at 2- and 3-positions is indole.

5. A process as claimed in claim 2 wherein the percarboxylic acid is a compound selected from the group consisting of peraliphatic acids and perbenzoic acid derivatives.

6. A process as claimed in claim 2 wherein the percarboxylic acid is peracetic acid or m-chloroperbenzoic acid.

7. A process as claimed in claim 2 wherein the percarboxylic acid is used in an amount of 0.01 to 100 moles per mole of the indole compound.

8. A process as claimed in claim 2 wherein the reaction temperature is in the range of −10° C. to 170° C.

9. A process as claimed in claim 2, wherein the reaction time is not longer than 50 hours wherein the percarboxylic acid is peracetic acid or m-chloroperbenzoic acid, wherein the percarboxylic acid is sued in an amount of 0.01 to 100 moles per mole of the indole compound, wherein the reaction temperature is in the range of −10° C. to 170° C., and wherein the indole compound having no substituent at 2- and 3-positions is indole.

10. A process as claimed in claim 2 wherein the formed indigo compound is recovered in the form of a solid according to a solid liquid separation technique.

11. A process as claimed in claim 1 wherein the liquid medium is an aprotic solvent and the reaction is carried out by heating over 60° C.

12. A process as claimed in claim 11 wherein the indole compound having no substituent at 2- and 3-positions is a compound selected from the group consisting of indole, alkylindoles, cycloalkylindoles, arylindoles, halogenated indoles, hydroxyindoles, alkoxyindoles, phenoxyindoles, halogenated alkylindoles, nitroindoles, acylindoles, acyloxyindoles, indolecarboxylic acids and esters thereof, N,N-dialkylaminoindoles and sulfonated indoles.

13. A process as claimed in claim 11 wherein the indole compound having no substituent at 2- and 3-positions is indole.

14. A process as claimed in claim 11 wherein the percarboxylic acid is a compound selected from the group consisting of peraliphatic acids and perbenzoic acid derivatives.

15. A process as claimed in claim 11 wherein the percarboxyalic acid is peracetic acid for m-chloroperbenzoic acid.

16. A process as claimed in claim 11 wherein the percarboxylic acid is used in an amount of 0.01 to 100 moles per mole of the indole compound.

17. A process as claimed in claim 11 wherein the aprotic solvent is a compound selected from the group consisting of aliphatic and alicyclic hydrocarbons, aromatic hydrocarbons, aliphatic and aromatic halogen compounds, ethers, ketones, esters, carbonates, aliphatic and aromatic nitro compounds, and nitriles.

18. A process as claimed in claim 11 wherein the reaction time is not longer than 50 hours.

19. A process as claimed in claim 11 wherein the formed indigo compound is recovered in the form of a solid according to a solid-liquid separation technique.

20. A process as claimed in claim 1 wherein the reaction is carried out in the presence of a metallic compound catalyst capable of oxidizing the carbon atom at the 3-position of the indole compound and/or in the presence of a promoter.

21. A process as claimed in claim 20 wherein the metallic compound catalyst is a compound of a metal selected from the group consisting of groups 4A, 5A and 6A of the periodic table, silver, aluminium, the iron group, the platinum group, and zinc.

22. A process as claimed in claim 20 wherein the metallic compound catalyst is a compound selected from the group consisting of compounds of titanium, vanadium, molybdenum and tungsten.

23. A process as claimed in claim 20 wherein the metallic compound catalyst is a compound of tungsten.

24. A process as claimed in claim 20 wherein the metallic compound catalyst is used in an amount of not greater than 0.5 mole per mole of the indigo compound.

25. A process as claimed in claim 20 wherein the promotor is a compound selected from the group consisting of compounds of dehydrating agents, radical scavengers, ligands of catalytic metals, boric acid esters and metaboric acid esters, salts of alkaline metals and alkaline earth metals, and salts of rare earth metals.

26. A process as claimed in claim 20 wherein the promoter is used in an amount of not greater than 50 moles per mole of the indigo compound.

27. In a process wherein an indole compound having no substituent at the 2- and 3-positions is reacted with a percarboxylic acid in the presence of a liquid medium, the improvement wherein the liquid medium is either an alcohol solvent for the indole compound or the reaction is conducted above 60° C. and the liquid medium is an aprotic solvent for the indole compound, thereby oxidizing the indole to the corresponding indigo compound, and recovering the thus-produced indigo compound.

28. The process of claim 27, wherein the thus-produced indigo compound precipitates from the reaction solvent and is recovered therefrom by a solid-liquid separation technique.

* * * * *